(12) United States Patent
Christensen et al.

(10) Patent No.: US 9,775,972 B2
(45) Date of Patent: Oct. 3, 2017

(54) INTERLOCKING NEEDLE HUB AND CATHETER HUB ACTUATOR TO INCREASE RIGIDITY OF IV CATHETER ASSEMBLY

(71) Applicant: Becton, Dickinson and Company, Franklin Lakes, NJ (US)

(72) Inventors: Corey M. Christensen, Salt Lake City, UT (US); Stephen T. Bornhoft, Midvale, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 206 days.

(21) Appl. No.: 13/954,511

(22) Filed: Jul. 30, 2013

(65) Prior Publication Data
US 2015/0038909 A1 Feb. 5, 2015

(51) Int. Cl.
A61M 5/178 (2006.01)
A61M 25/06 (2006.01)
A61M 25/00 (2006.01)
A61M 39/22 (2006.01)

(52) U.S. Cl.
CPC ...... *A61M 25/0606* (2013.01); *A61M 25/008* (2013.01); *A61M 25/0097* (2013.01); *A61M 25/0625* (2013.01); *A61M 25/0631* (2013.01); *A61M 2039/226* (2013.01); *A61M 2205/10* (2013.01)

(58) Field of Classification Search
CPC .......... A61M 25/0097; A61M 25/0606; A61M 25/0625; A61M 25/0631
USPC ..................................................... 604/164.07
See application file for complete search history.

(56) References Cited

U.S. PATENT DOCUMENTS

| 5,156,596 | A | * | 10/1992 | Balbierz | 604/164.11 |
| 5,391,152 | A | * | 2/1995 | Patterson | A61M 25/0606 604/165.04 |
| 5,772,643 | A | * | 6/1998 | Howell | 604/533 |
| 6,213,978 | B1 | * | 4/2001 | Voyten | A61M 25/0606 604/164.01 |
| 7,008,404 | B2 | * | 3/2006 | Nakajima | 604/158 |

(Continued)

FOREIGN PATENT DOCUMENTS

| DE | 20 2009 009602 U1 | 12/2009 |
| EP | 0 268 480 A1 | 5/1988 |
| WO | WO 2009/091514 A2 | 7/2009 |

*Primary Examiner* — Kevin C Sirmons
*Assistant Examiner* — Leah Swanson
(74) *Attorney, Agent, or Firm* — Jeanne Lukasavage; Kirton McConkie; Craig Metcalf

(57) ABSTRACT

The present invention extends to a design of a needle hub and an actuator of a catheter assembly that allows the needle hub and actuator to interlock within the catheter hub. This interlocking allows the needle hub to be inserted into the catheter hub thereby increasing the rigidity of the catheter assembly. The interlocking can be accomplished by forming channels in the proximal end of the actuator and corresponding protrusions from the distal end of the needle hub. In some embodiments, the channels and protrusions can be formed at the top and bottom of the catheter hub and needle hub respectively to thereby increase the vertical rigidity of the catheter assembly. The increase in vertical rigidity can prevent flexing of the catheter hub with respect to the needle shield when a downward force is applied to the catheter assembly such as is common during insertion of the needle.

19 Claims, 14 Drawing Sheets

(56) References Cited

U.S. PATENT DOCUMENTS

2003/0083621 A1\* 5/2003 Shaw ................ A61M 25/0631
                                                604/164.07
2009/0005741 A1\* 1/2009 Martin .............. A61M 25/0069
                                                604/256
2010/0204660 A1    8/2010 McKinnon et al.

\* cited by examiner

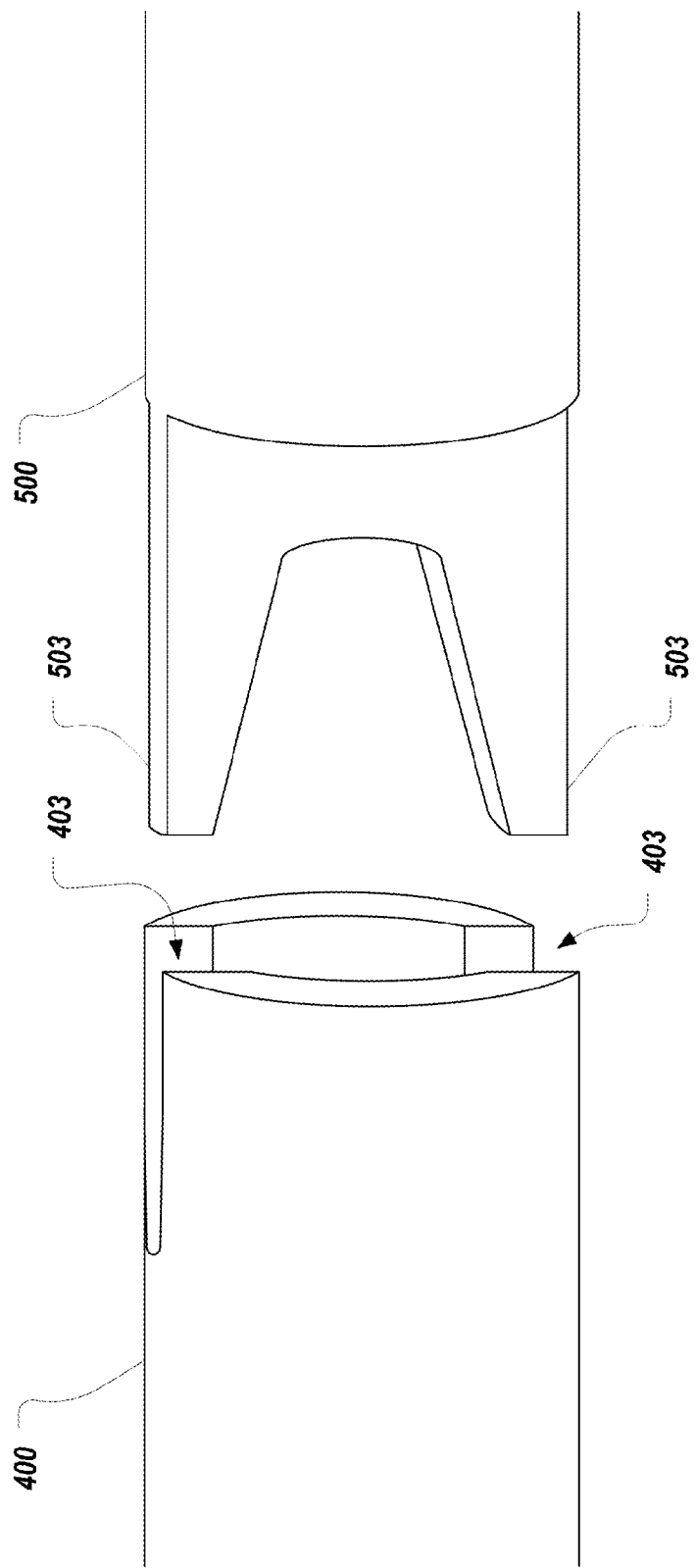

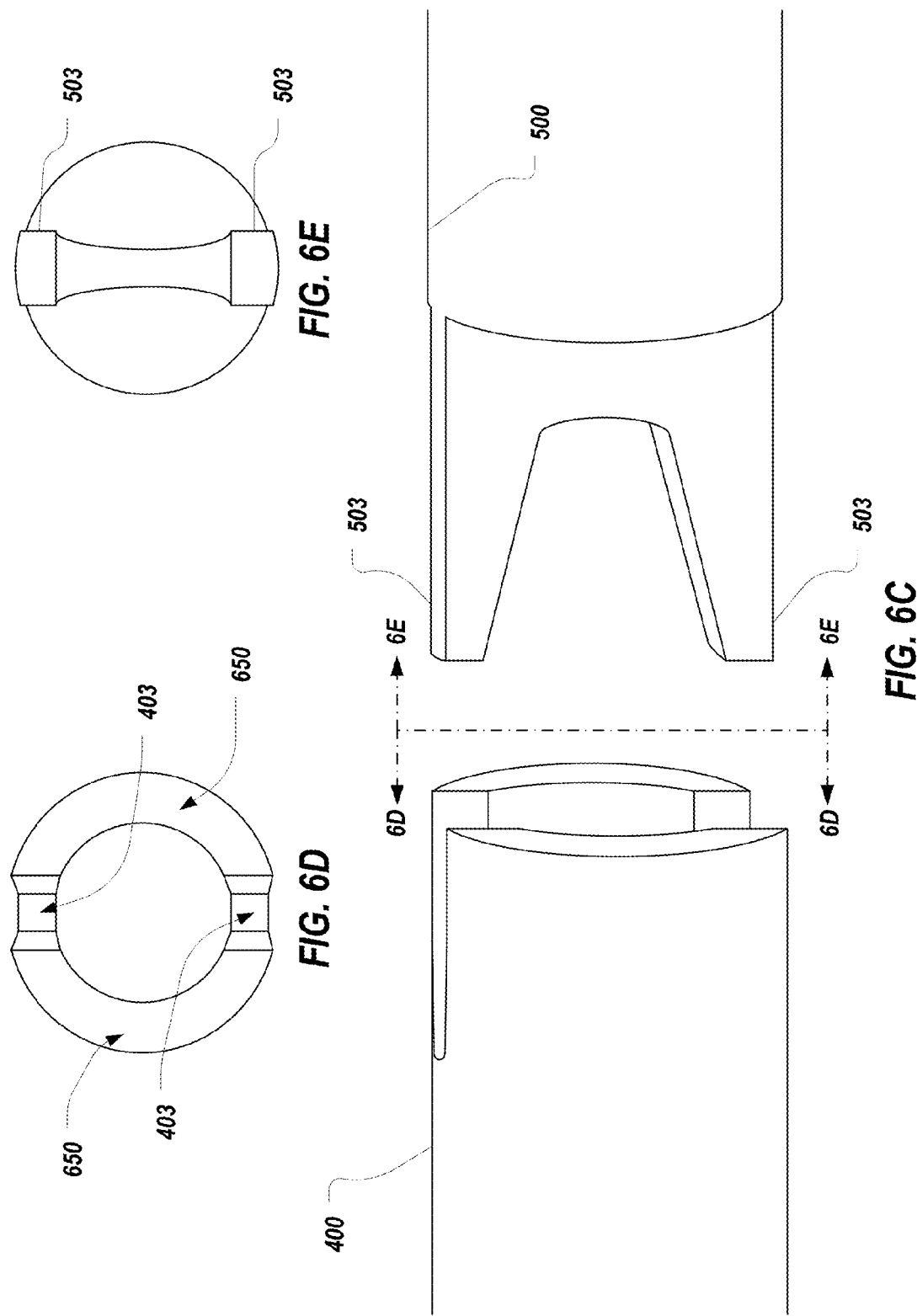

INTERLOCKING NEEDLE HUB AND CATHETER HUB ACTUATOR TO INCREASE RIGIDITY OF IV CATHETER ASSEMBLY

BACKGROUND OF THE INVENTION

The present invention relates generally to intravenous (IV) catheter assemblies and particularly to increasing the rigidity between a catheter hub and a needle shield of the assembly to facilitate the threading of the catheter.

FIG. 1 illustrates a common IV catheter assembly 100 that consists of a catheter hub 101 and a needle shield 103. Needle shield 103 contains a needle hub from which a needle 102 extends. Needle 102 extends through catheter hub 101 and is used to thread the catheter into the vasculature of a patient. IV catheter assembly 100 is initially handled by a clinician as a single component. The clinician inserts needle 102 into the patient's vasculature and then slides the catheter over top of the needle further into the vasculature. Once the catheter is placed appropriately in the vasculature, needle 102 can be retracted into needle shield 103. Then, needle shield 103 can be detached from catheter hub 101 leaving catheter hub 101 for connection of other devices for blood draw or fluid injection.

Because needle shield 103 and catheter hub 101 are separate components, a certain amount of flexibility may exist between the two components. If this amount of flexibility is too great, the clinician may experience difficulty when inserting needle 102 into the patient's vasculature.

Typically, catheter hub 101 is configured at a proximal end with a connector that is designed to receive a standard connector of another device. For example, catheter hub 101 is often configured to receive a male luer of another device. Because of this, there are limited options for reinforcing the connection between catheter hub 101 and needle shield 103 to limit the amount of flexibility between the components when needle 102 is inserted. Any structural reinforcements must be made in such a way that other devices (e.g. male luers) will still be attachable to catheter hub 101.

Also, many catheter hubs employ a blood control valve that includes components positioned inside of the catheter hub. For example, a catheter hub may include an actuator that is initially positioned near the proximal end of the catheter hub on one side of a septum, and is then forced distally through the septum to open a fluid path through the catheter hub. Because the actuator is positioned near the proximal end of the catheter hub, there is little area for providing structural reinforcements inside the catheter hub.

FIGS. 2A and 2B illustrate an example of a catheter assembly 200 that includes a blood control valve. Catheter assembly 200 includes a catheter hub 201 that employs an actuator 207 and a needle shield 203. Needle shield 203 contains a needle hub 204 which contains a needle 205. Actuator 207 is designed to be forced through septum 206 when another access device is connected to catheter hub 201 to thereby open a fluid pathway through catheter hub 201. Because of the presence of actuator 207 within catheter hub 201, there is little or no additional space within catheter hub 201 into which needle hub 204 could extend.

Also, because actuator 207 is forced through septum 206 by access devices that are connected to catheter hub 201, actuator 207 must have a proximal end that the access devices can press against as the access devices are connected to catheter hub 201. Accordingly, the proximal end of actuator 207 is typically larger in size (e.g. as shown in FIGS. 2A and 2B) which further minimizes the amount of space available at the proximal end of catheter hub 201.

As shown in FIG. 2A, catheter hub 201 and needle shield 203 are connected so that the components are coaxially aligned. In contrast, FIG. 2B illustrates the state of catheter assembly 200 while a clinician is handling the assembly to insert needle 205 into a patient's vasculature. As shown, the clinician typically grips assembly 200 and applies a downward (as represented by the arrow) and forward force to propel needle 205 through the patient's skin. This downward force causes catheter hub 201 and needle shield 203 to flex relative to each other as represented by the dashed line in FIG. 2B.

A substantial amount of flexing may occur because the pivot point between catheter hub 201 and needle shield 203 is formed where the two components connect. Because of this, the primary structure that resists flexing is the portion of needle shield 203 that extends into catheter hub 201. Because this portion is relatively short and thin, it cannot provide significant strength to withstand the flexing forces. As a result, an undesirable amount of flexing often occurs.

The flexing between the catheter hub and the needle shield creates various problems. Primarily, when the components flex, the amount of force transferred to the needle is reduced thereby making it more difficult to insert the needle through the patient's skin. Also, when this flexing occurs, the clinician perceives the components as being weak which may cause the clinician to alter the catheter insertion procedure or to view the catheter assembly as being unsatisfactory. In some cases, this flexing may also lead to failure of the components.

BRIEF SUMMARY OF THE INVENTION

The present invention extends to a design of a needle hub and an actuator of a catheter assembly that allows the needle hub and actuator to interlock within the catheter hub. This interlocking allows the needle hub to be inserted into the catheter hub thereby increasing the rigidity of the catheter assembly. The interlocking can be accomplished by forming one or more channels in the proximal end of the actuator and one or more corresponding protrusions that extend from the distal end of the needle hub. In some embodiments, the channels and protrusions can be formed at the top and bottom of the catheter hub and needle hub respectively to thereby increase the vertical rigidity of the catheter assembly. The increase in vertical rigidity can prevent flexing of the catheter hub with respect to the needle shield when a downward force is applied to the catheter assembly such as is common during insertion of the needle.

In some embodiments, the present invention is implemented as a catheter assembly comprising a catheter hub and a needle shield. The catheter hub contains an actuator and a septum. The actuator is configured to pierce the septum when a force is applied to the actuator. The needle shield is connected to the catheter hub and contains a needle hub. The needle hub contains a needle that extends through the catheter hub. The needle hub also includes one or more protrusions that extend from a distal end of the needle hub while the actuator includes one or more channels that extend from a proximal end and into the actuator. The one or more protrusions of the needle hub insert into the one or more channels thereby interlocking the needle hub with the actuator to provide greater rigidity between the catheter hub and the needle shield.

In some embodiments, the actuator includes two channels and the needle hub includes two protrusions. These channels can be positioned at the top and bottom of the actuator to provide greater rigidity against vertical forces applied to the catheter assembly.

In some embodiments, the actuator is positioned completely within the catheter hub such that the needle hub extends into the catheter hub to interlock with the actuator.

In some embodiments, the protrusions extend distally from the outer diameter of the needle hub. The outer diameter of the protrusions can also match the outer diameter of the channels. In some embodiments, the protrusions extend into the catheter hub.

In some embodiments, the catheter assembly is an intravenous catheter assembly where the needle shield is detachable from the catheter hub to allow another access device to be connected to the catheter hub.

In other embodiments, the present invention is implemented as an actuator for use within a catheter hub. The actuator comprises a main body extending from a distal end to a proximal end. The distal end is configured to pierce a septum when a force is applied to the proximal end. The proximal end includes one or more channels that extend towards the distal end. The one or more channels are sized and shaped to receive one or more protrusions of a needle hub contained within a needle shield to thereby interlock the actuator and the needle hub to provide greater rigidity between the catheter hub and the needle shield.

In some embodiments, the proximal end of the actuator includes two channels. The two channels may be positioned at the top and bottom of the proximal end to provide greater rigidity against vertical forces.

In some embodiments, the actuator is positioned completely within the catheter hub such that, when a needle shield is attached to the catheter hub, a needle hub within the needle shield extends into the catheter hub to interlock with the actuator.

In some embodiments, the outer diameter of the channels matches the outer diameter of corresponding protrusions in a needle hub. In some embodiments, the one or more channels extend from the proximal end of the actuator.

In other embodiments, the present invention is implemented as a needle hub for use within a needle shield. The needle hub comprises a main body extending from a distal end to a proximal end. The main body contains a needle that extends out from the distal end. The distal end is configured with one or more protrusions that extend distally from the distal end. The one or more protrusions are configured to be inserted into corresponding channels formed in an actuator of a catheter hub.

In some embodiments, the one or more protrusions comprise two protrusions. The two protrusions may be positioned at the top and bottom of the distal end. The one or more protrusions may extend into the catheter hub in which the actuator is contained. In some embodiments, the protrusions extend distally from the outer diameter of the needle hub.

This summary is provided to introduce a selection of concepts in a simplified form that are further described below in the detailed description. This summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 6A illustrates a perspective view of an actuator having channels and a needle hub having protrusions in which the actuator and needle hub are in an unlocked position;

FIG. 6C illustrates the perspective view of the actuator and needle hub of FIG. 6A with indications of views provided in FIGS. 6D and 6E;

FIG. 6D illustrates a right side view of the actuator of FIG. 6C;

FIG. 6E illustrates a left side view of the needle hub of FIG. 6C;

DETAILED DESCRIPTION OF THE INVENTION

Figure 1:
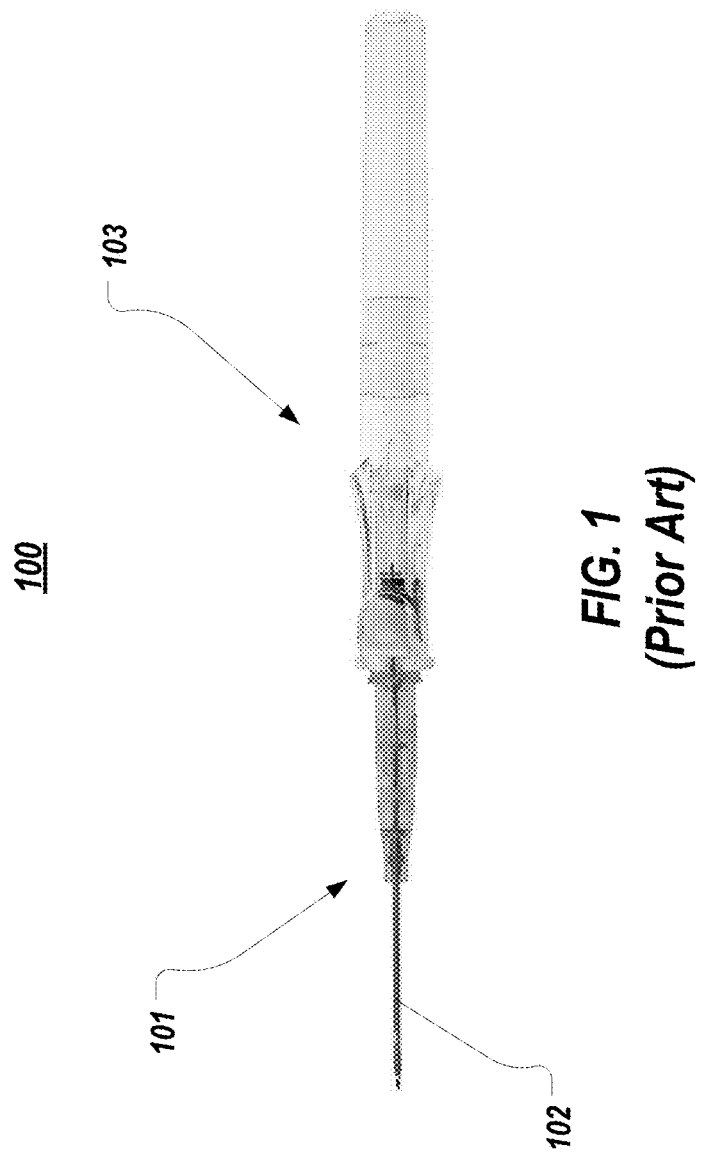
FIG. 1 illustrates a prior art intravenous catheter assembly within which an actuator and needle hub configured according to embodiments of the present invention can be used to increase the rigidity of the catheter assembly in one or more directions.

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

The present invention extends to a design of a needle hub and an actuator of a catheter assembly that allows the needle hub and actuator to interlock within the catheter hub. This interlocking allows the needle hub to be inserted into the catheter hub thereby increasing the rigidity of the catheter assembly. The interlocking can be accomplished by forming one or more channels in the proximal end of the actuator and one or more corresponding protrusions that extend from the distal end of the needle hub. In some embodiments, the channels and protrusions can be formed at the top and bottom of the catheter hub and needle hub respectively to thereby increase the vertical rigidity of the catheter assembly. The increase in vertical rigidity can prevent flexing of the catheter hub with respect to the needle shield when a downward force is applied to the catheter assembly such as is common during insertion of the needle.

In some embodiments, the present invention is implemented as a catheter assembly comprising a catheter hub and a needle shield. The catheter hub contains an actuator and a septum. The actuator is configured to pierce the septum when a force is applied to the actuator. The needle shield is connected to the catheter hub and contains a needle hub. The needle hub contains a needle that extends through the catheter hub. The needle hub also includes one or more protrusions that extend from a distal end of the needle hub while the actuator includes one or more channels that extend from a proximal end and into the actuator. The one or more protrusions of the needle hub insert into the one or more channels thereby interlocking the needle hub with the actuator to provide greater rigidity between the catheter hub and the needle shield.

In other embodiments, the present invention is implemented as an actuator for use within a catheter hub. The actuator comprises a main body extending from a distal end to a proximal end. The distal end is configured to pierce a septum when a force is applied to the proximal end. The proximal end includes one or more channels that extend towards the distal end. The one or more channels are sized and shaped to receive one or more protrusions of a needle hub contained within a needle shield to thereby interlock the actuator and the needle hub to provide greater rigidity between the catheter hub and the needle shield.

In other embodiments, the present invention is implemented as a needle hub for use within a needle shield. The needle hub comprises a main body extending from a distal end to a proximal end. The main body contains a needle that extends out from the distal end. The distal end is configured with one or more protrusions that extend distally from the distal end. The one or more protrusions are configured to be inserted into corresponding channels formed in an actuator of a catheter hub.

Figure 3A:
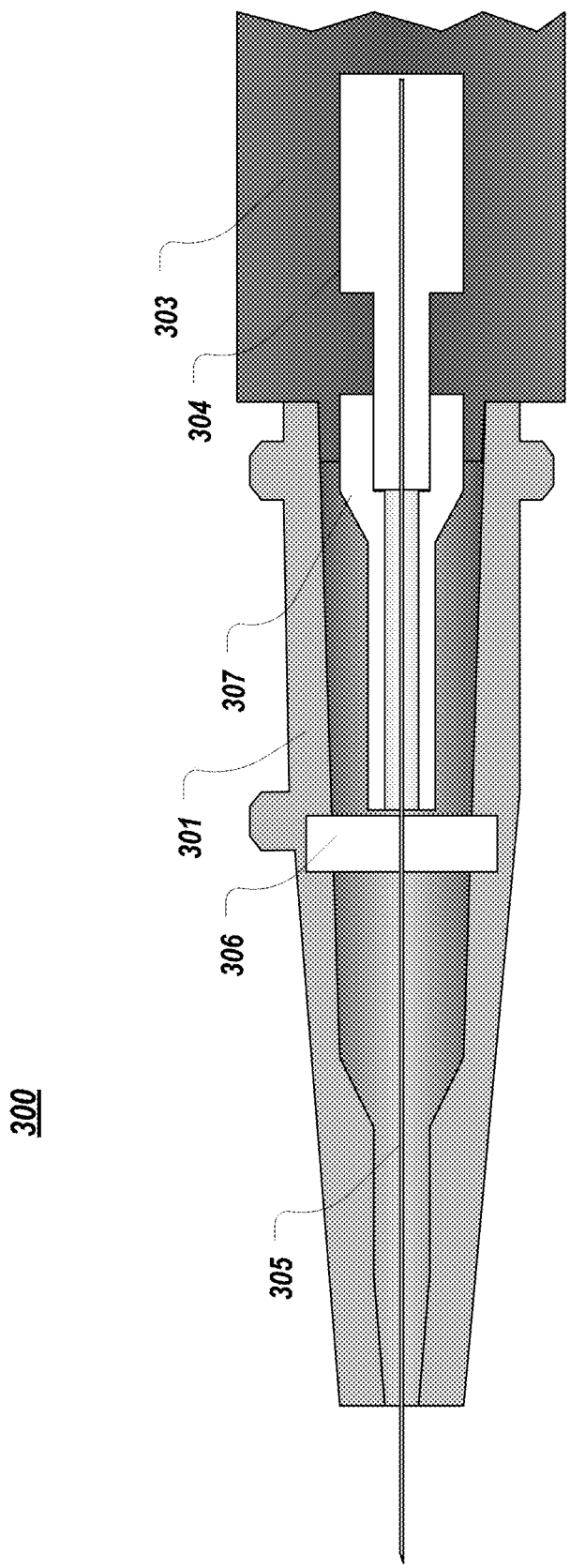
FIG. 3A illustrates a cross-sectional view of a catheter assembly that includes an actuator and needle hub configured in accordance with one or more embodiments of the invention.
Figure 3B:
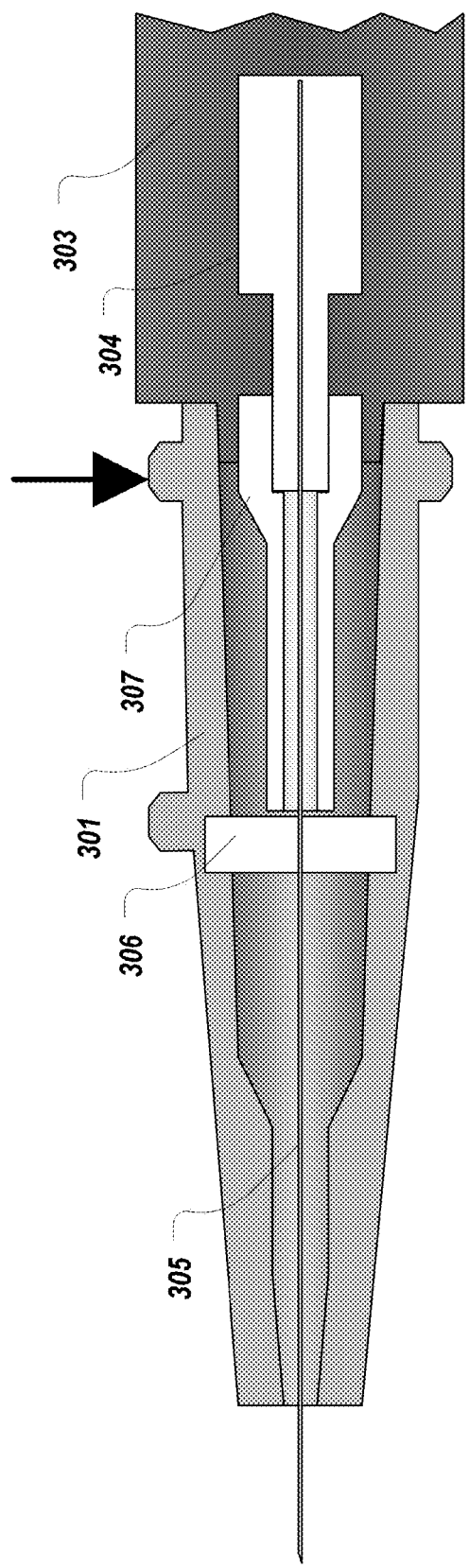
FIG. 3B illustrates a cross-sectional view of the catheter assembly of FIG. 2A in which a downward force is applied to the catheter assembly without causing flexing between the catheter hub and needle shield due to the interlocking actuator and needle hub.

FIGS. 3A and 3B illustrate a catheter assembly 300 in accordance with one or more embodiments of the invention. Catheter assembly 300 includes a catheter hub 301 that interconnects with a needle shield 303. Catheter hub 301 includes a septum 306 and an actuator 307 for piercing septum 306 when another access device is connected to catheter hub 301. Needle shield 303 includes a needle hub 304 that contains a needle 305. Once needle 305 has been used to insert a catheter into a patient's vasculature, needle hub 304 can be retracted further into needle shield 303 so that needle 305 is fully contained within needle shield 303. Needle shield 303 can then be disconnected from catheter hub 301 to allow other access devices to be connected to catheter hub 301.

As shown, actuator 307 and needle hub 304 are configured to interlock. In this way, needle hub 304 can insert into actuator 307. This interlocking provides greater rigidity between catheter hub 301 and needle shield 303. Specifically, because needle hub 304 extends into actuator 307, the amount of flexing that can occur between catheter hub 301 and needle shield 303 is reduced. FIG. 3B depicts that a downward force (as represented by the arrow) causes minimal flexing between catheter hub 301 and needle shield 303. This reduced amount of flexing will cause more force to be transferred to needle 305 during the needle insertion process and will provide the clinician with a better feel.

Figure 3C:
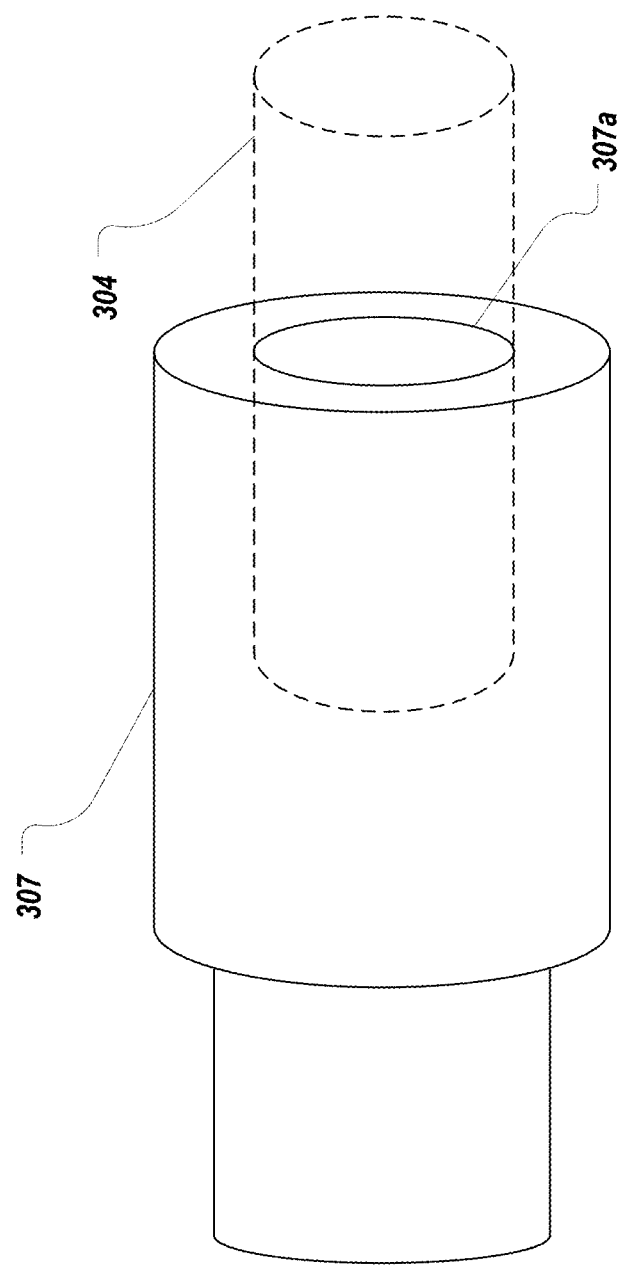
FIG. 3C illustrates a perspective view of a portion of an actuator and needle hub to illustrate one particular way in which the actuator and needle hub can be interlocked to increase the rigidity of a catheter assembly.

FIG. 3C illustrates a perspective view of one example of how actuator 307 and needle hub 304 can interlock. As shown, actuator 307 can include an opening 307a at its proximal end that is sufficiently large to allow the distal end of needle hub 304 to insert into the opening. In some implementations, this configuration can provide an increased amount of rigidity between catheter hub 301 and needle shield 303.

However, in some cases, this configuration creates additional difficulties. In many cases, in order to have an opening 307a that is sufficiently large to allow needle hub 304 to extend sufficiently into actuator 307, the outer wall of actuator 307 around opening 307a becomes too narrow to provide an adequate surface against which another access device can press to force actuator 307 through septum 306. For example, the outer wall can be required to be so narrow that another access device does not contact the outer wall when the access device is connected to catheter hub 301. Similarly, the outer wall can be so narrow that it lacks sufficient strength to withstand the force necessary to force actuator 307 through septum 306. Accordingly, in many implementations, the design shown in FIG. 3C will not be preferred.

Figure 4:
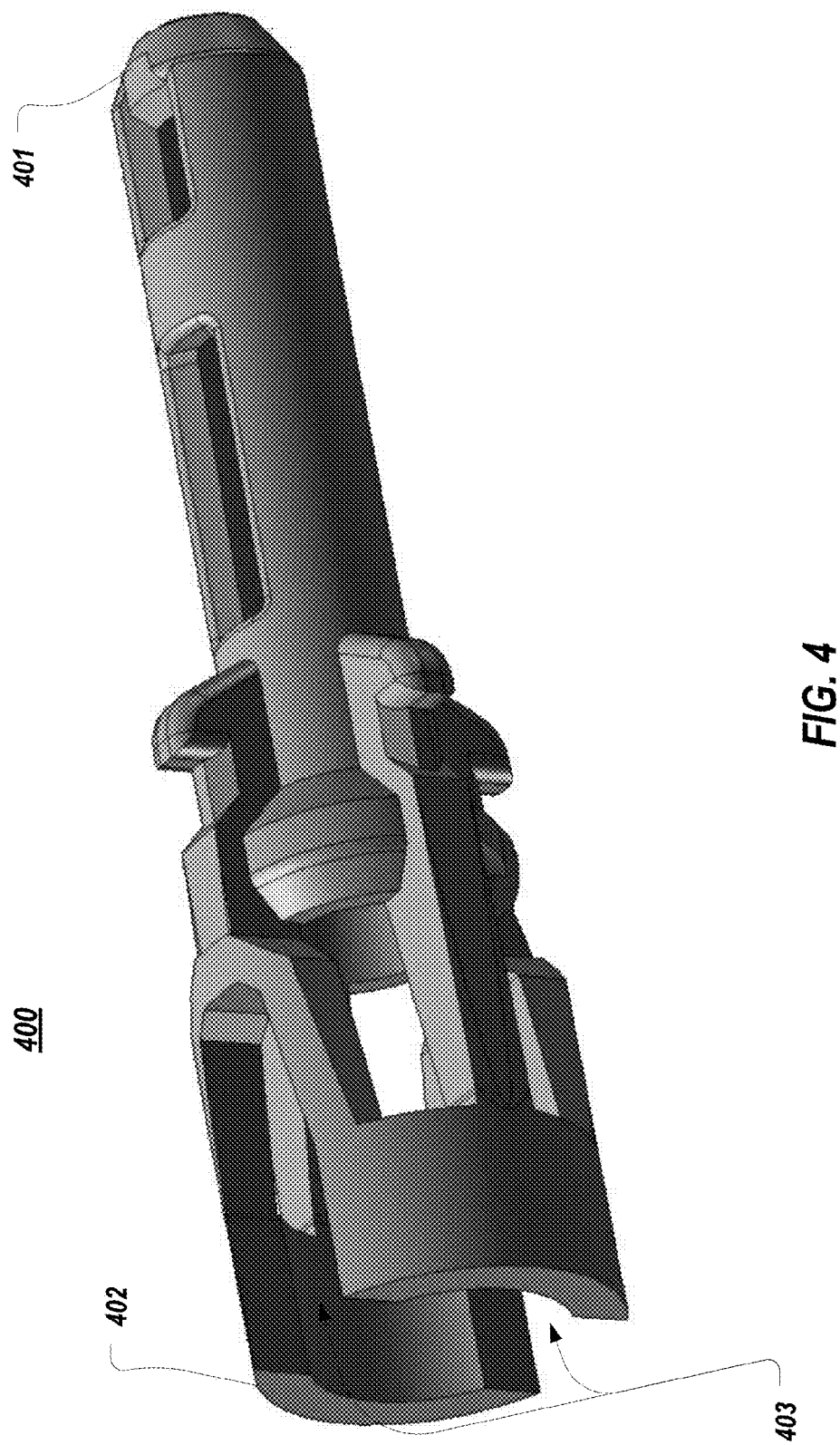
FIG. 4 illustrates a perspective view of an example of an actuator that includes channels formed at the top and bottom of the proximal end of the actuator which provide an interface for interlocking with protrusions of a needle hub.
Figure 5:
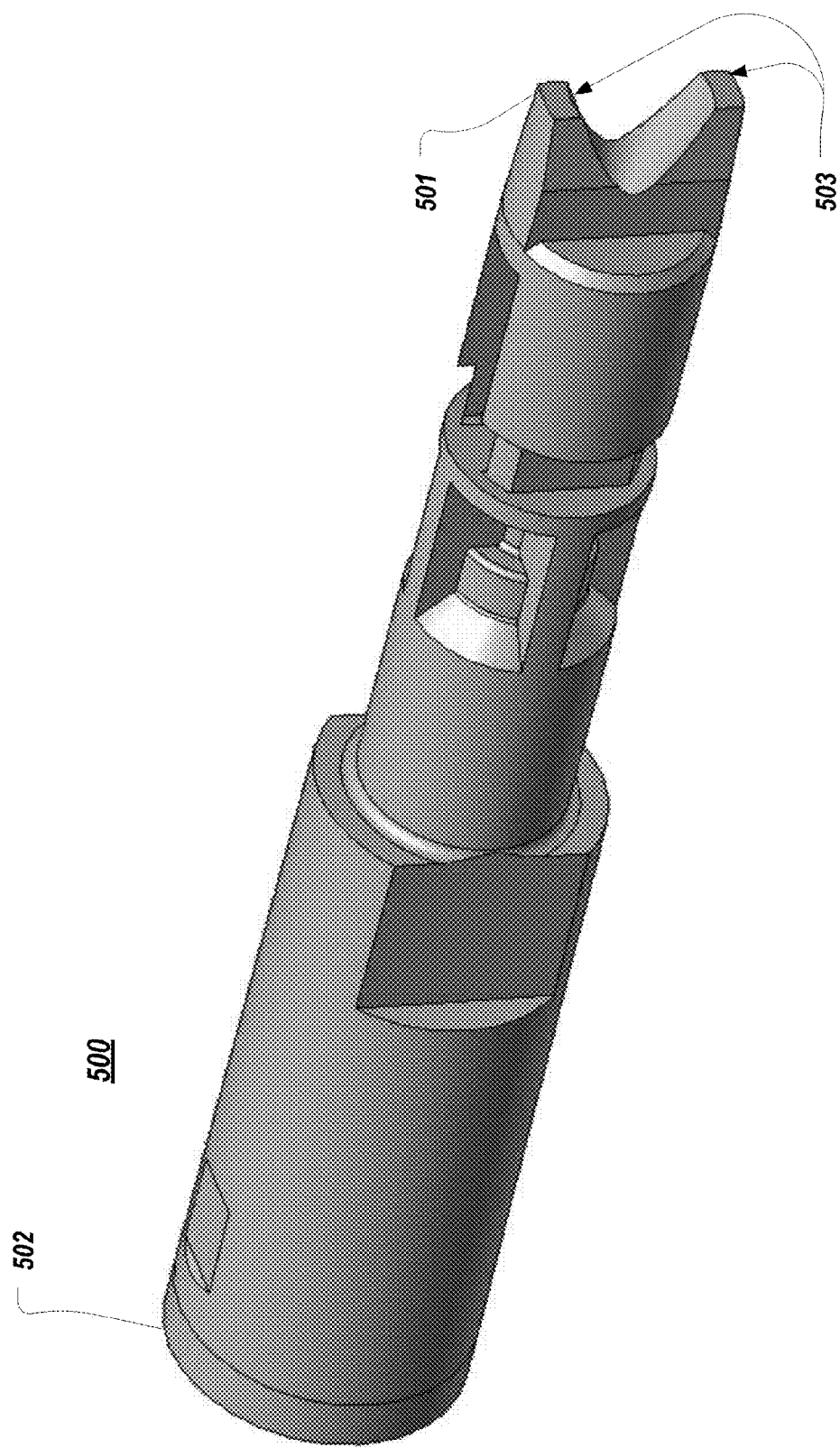
FIG. 5 illustrates a perspective view of an example of a needle hub that includes protrusions formed at the top and bottom of the distal end of the needle hub which provide an interface for interlocking with channels of an actuator.

FIGS. 4 and 5 illustrate another configuration of an actuator 400 and needle hub 500 respectively which can be employed to increase the rigidity between the catheter hub and needle shield without sacrificing the structural integrity of the actuator. As shown in FIG. 4, actuator 400 includes a proximal end 402 and a distal end 401. Proximal end 402 is configured to be contacted by an access device when the access device is attached to the catheter hub so that actuator 400 is forced through a septum by the access device.

Proximal end 402 has a generally circular shape which provides the area against which the access device applies a force. However, to allow needle hub 500 to interlock with actuator 400 without sacrificing the structural integrity of actuator 400, two channels 403 are formed within proximal end 402. Channels 403 are formed at the top and bottom of actuator 400. The purpose of positioning channels 403 in this manner will be described below after needle hub 500 is described. Even with channels 403, a substantial amount of proximal end 402 remains to provide a contact area against which an access device can press to force actuator 400 through the septum and to provide structural integrity to actuator 400.

As shown in FIG. 5, needle hub 500 includes a proximal end 502 and a distal end 501. Distal end 501 includes protrusions 503. Protrusions 503 are positioned at the top and bottom of needle hub 500 and are shaped to conform to channels 403 formed in actuator 400. Accordingly, protrusions 503 can insert into channels 403 to interlock actuator 400 and needle hub 500.

Channels 403 and protrusions 503 are positioned at the top and bottom of the respective components to provide reinforcement in the vertical direction. Because the flexing between the catheter hub and needle shield is primarily due to the downward force applied by the clinician during needle insertion, the positioning of channels 403 and protrusions 503 at the top and bottom provides support against the downward force thereby minimizing the amount of flexing that can occur between the catheter hub and needle shield. Although this design may not provide substantial increases in the rigidity of the components in the horizontal direction, such rigidity in the horizontal direction is generally not critical because it is oftentimes not desired to apply a horizontal force to the catheter assembly during needle insertion.

Figure 6B:
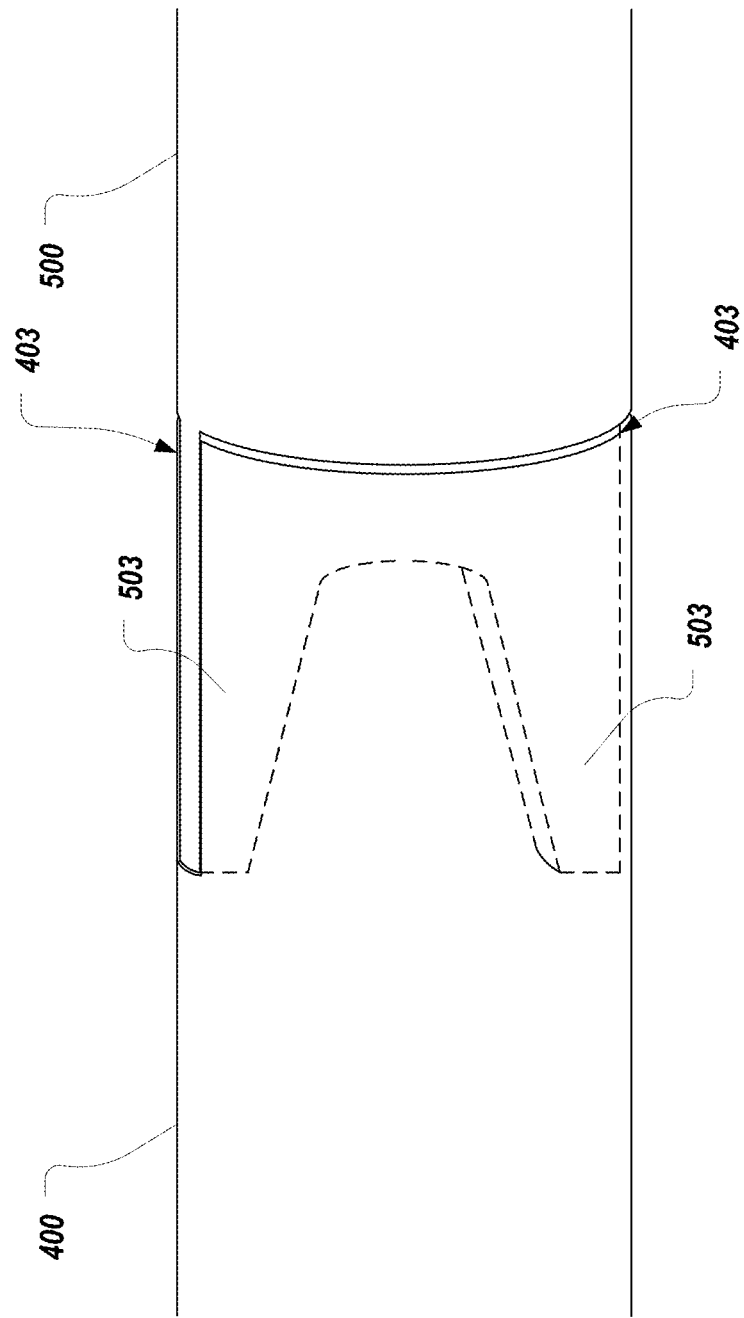
FIG. 6B illustrates a perspective view of the actuator and needle hub of FIG. 6A in which the actuator and needle hub are in an interlocked position.

FIGS. 6A and 6B provide a perspective view of actuator 400 and needle hub 500 in an unlocked and an interlocked configuration respectively. In FIG. 6A, needle hub 500 is adjacent to, but not inserted into, actuator 400. As shown, protrusions 503 are configured to match the general shape of channels 403. In FIG. 6B, needle hub 500 is shown as having been inserted into actuator 400 such that protrusions 503 are interlocked with channels 403.

FIG. 6C again illustrates actuator 400 and needle hub 500 in an unlocked configuration with the indications of the side views shown in FIGS. 6D and 6E. In FIG. 6D, a right side view of actuator 400 is shown while in FIG. 6E a left side view of needle hub 500 is shown. As shown in FIG. 6D, channels 403 are positioned at the top and bottom of actuator 400. Similarly, in FIG. 6E, protrusions 503 are shown at the top and bottom of needle hub 500 corresponding to the position of channels 403.

Although actuator 400 and needle hub 500 are shown having two channels 403 and two protrusions 503 respectively, an actuator and needle hub can be configured with one or more channels and protrusions respectively. For example, in some embodiments, an actuator can have a single channel at the top while the corresponding needle hub has a single protrusion at the top. This configuration could still provide an increase in rigidity between the catheter hub and the needle shield, but in many cases will not be as effective as when two channels and protrusions are used.

Similarly, in some embodiments, an actuator can include more than two channels (e.g. two channels positioned on the left and right side in additional to the channels 403 shown in FIG. 6D). In such cases, the needle hub can include corresponding protrusions. This configuration would provide additional rigidity in the horizontal direction if such rigidity is desired. However, as stated above, if an excessive number of channels are formed within the actuator, the structural integrity of the actuator can be compromised. Accordingly, even though more than two channels/protrusions can be used, in preferred embodiments, the actuator includes two channels as has been described.

Referring again to FIG. 6D, the portions of the proximal end 402 of actuator 400 that extend between channels 403 are labeled as 650. Portions 650 form the surface area against which another access device applies a force to actuator 400 to force actuator 400 through the septum. As shown, even with channels 403, a substantial amount of surface area remains to provide adequate structural integrity to actuator 400 to receive such forces. Also, because channels 403 and protrusions 503 are used, the interlocking is accomplished while portions 650 remain positioned near the proximal end of the catheter hub. Having portions 650 near the proximal end of the catheter hub is important to ensure that actuator 400 will be forced through the septum when another access device is connected to the catheter hub.

The size of channels 403 (and as a result, the size of protrusions 503) can be selected to maximize the rigidity between the catheter hub and needle shield without sacrificing the structural integrity of actuator 400. This size can vary depending on the type of material from which actuator 400 is made, the intended use of a catheter assembly employing actuator 400 such as the types of access devices that will be attached to the catheter hub, etc.

The number of channels formed in actuator 400 can also be based on such considerations. For example, in some cases, it may be more desirable to provide greater rigidity to the catheter assembly in the horizontal direction than to maintain a certain level of structural integrity within the actuator. For example, in some cases, it may be necessary to apply downward and sideward forces to the catheter adapter during needle insertion. In such cases, an actuator having channels on the sides can be used to increase rigidity in the horizontal direction as well.

Figure 2A:
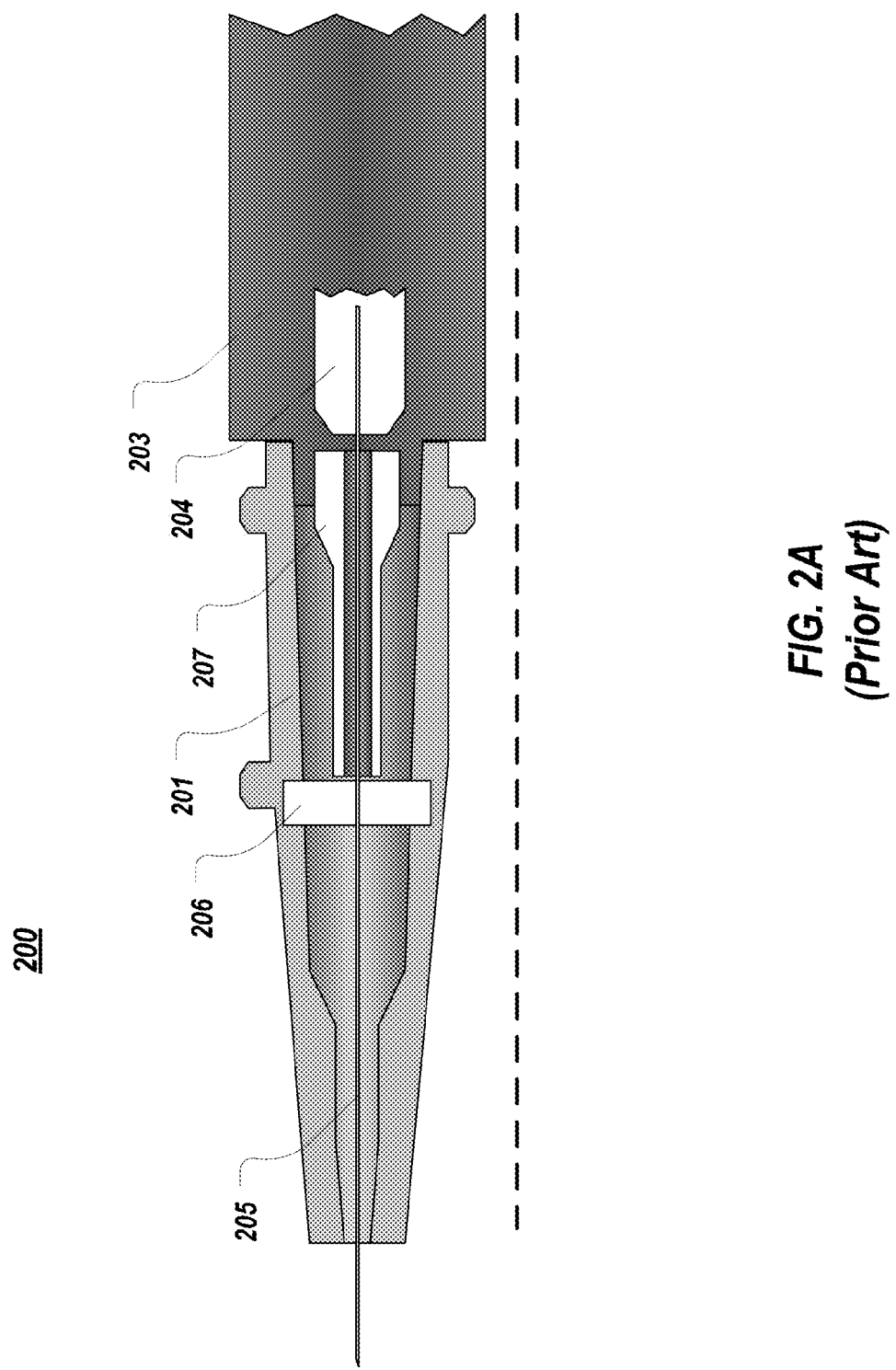
FIG. 2A illustrates a cross-sectional view of a prior art intravenous catheter assembly that includes an actuator for piercing a septum and a needle hub.
Figure 2B:
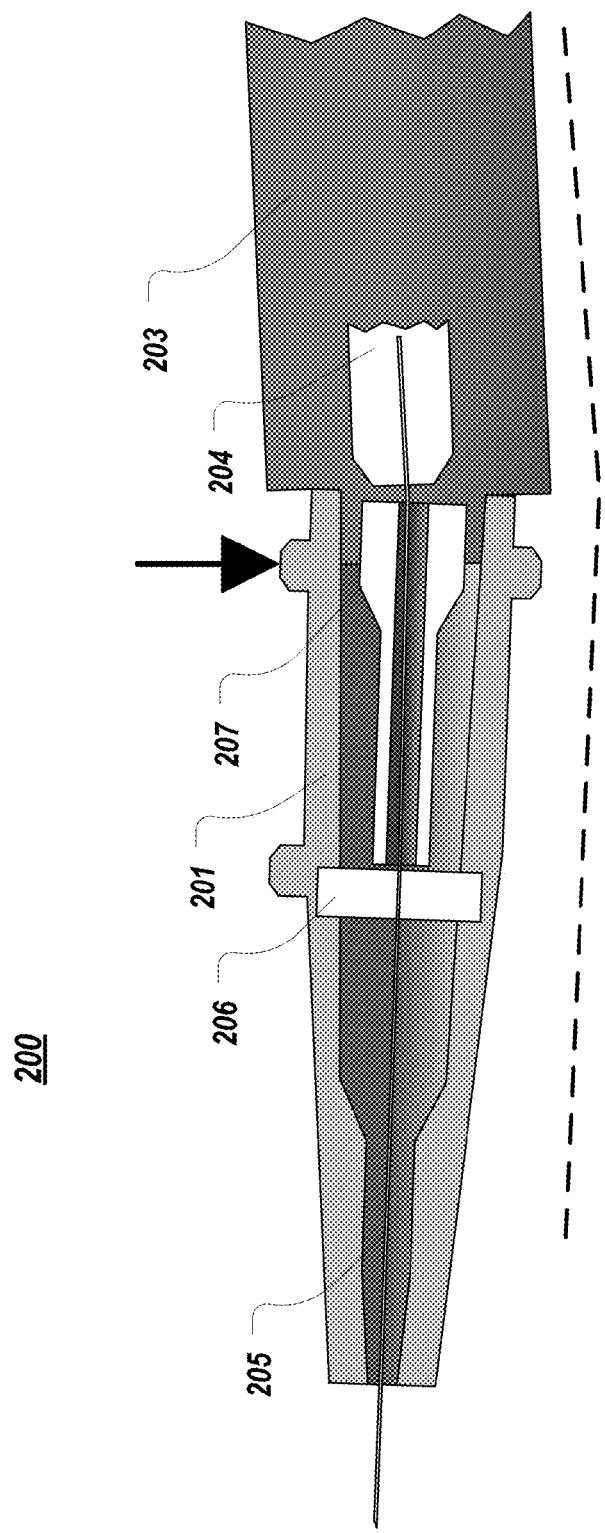
FIG. 2B illustrates a cross-sectional view of the prior art intravenous catheter assembly of FIG. 2A in which the flexing between the catheter hub and needle shield caused by a downward force is depicted.
Figure 7A:
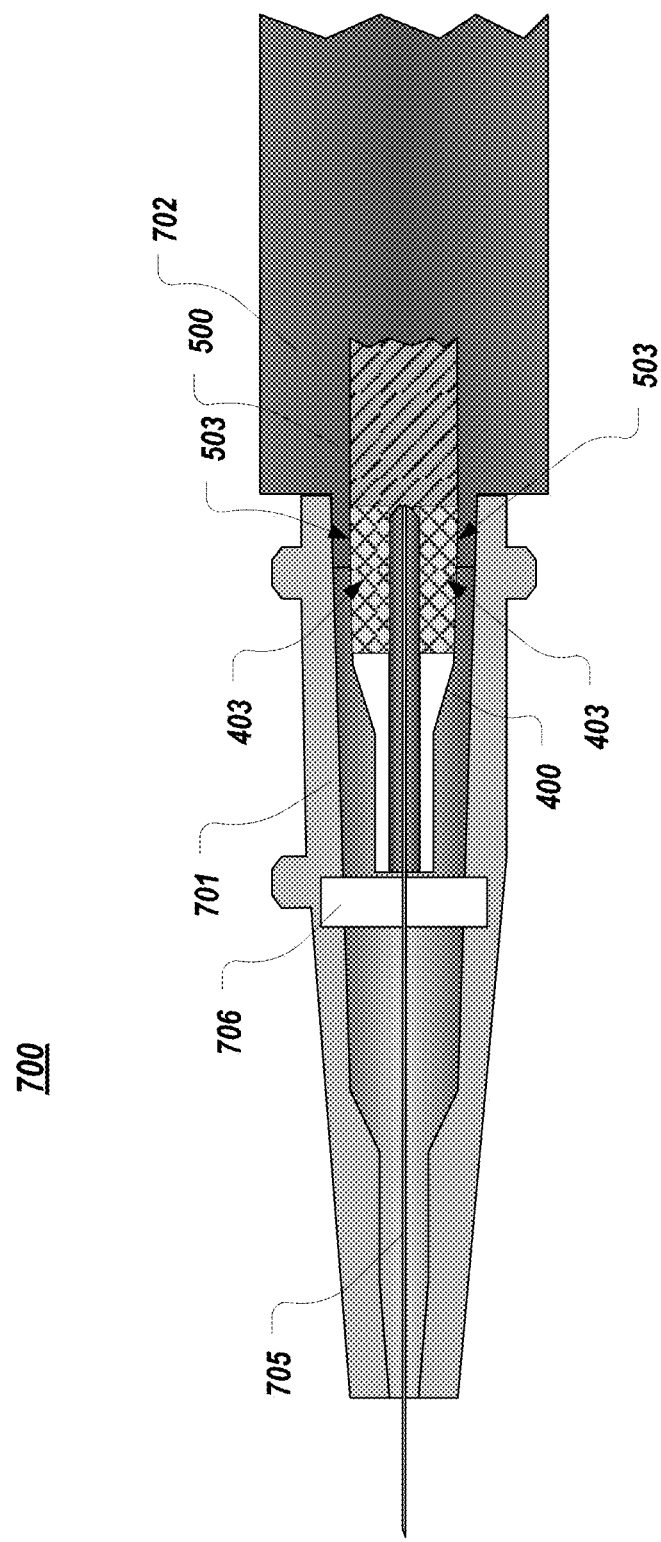
FIG. 7A illustrates a cross-sectional view of a catheter assembly that includes an actuator having two channels and needle hub having two protrusions in which the actuator and needle hub are interlocked.
Figure 7B:
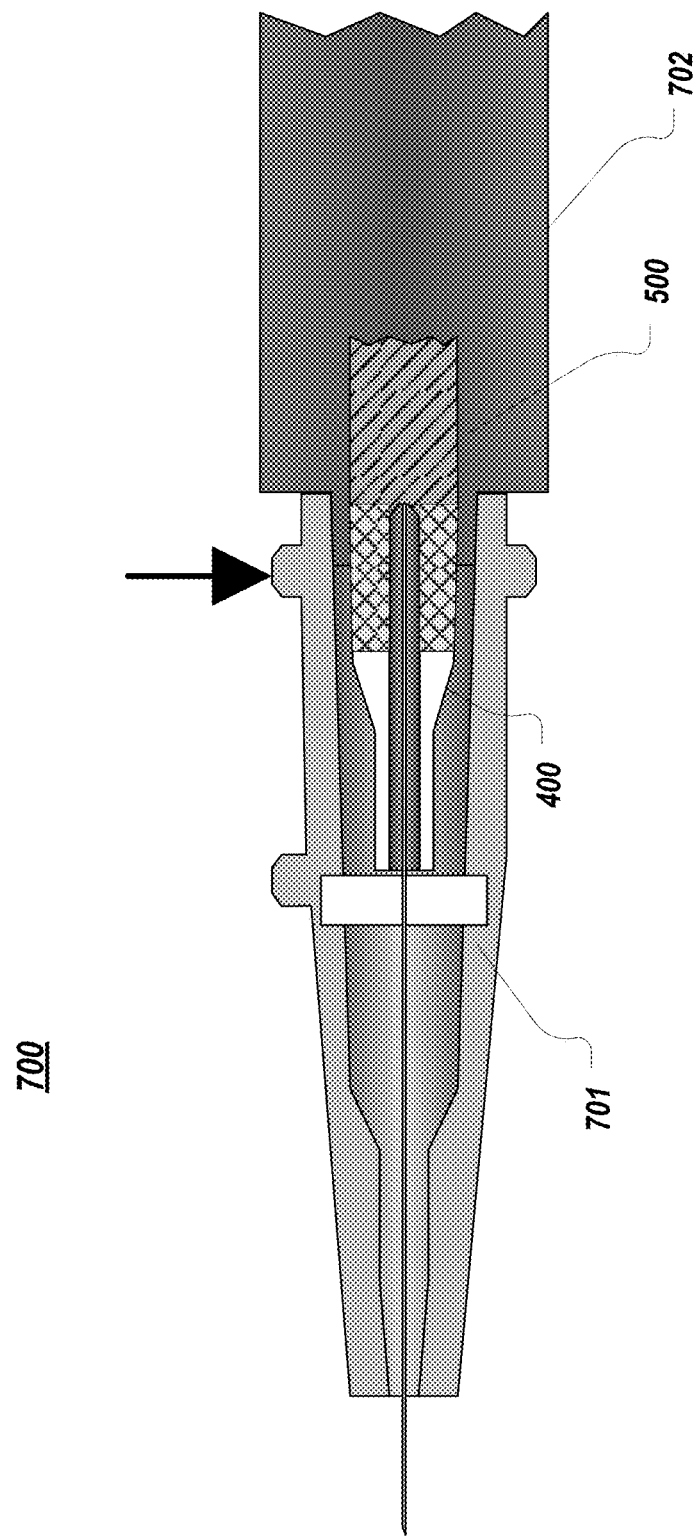
FIG. 7B illustrates a cross-sectional view of the catheter assembly of FIG. 7A in which no flexing occurs between the catheter hub and needle shield while a downward force is applied to the catheter assembly.

FIGS. 7A and 7B depict a cross-sectional view of a catheter assembly 700 that is similar to catheter assembly 200 of FIGS. 2A and 2B. However, catheter assembly 700 includes actuator 400 and needle hub 500. As shown, actuator 400 includes channels 403 (represented by lines running upwards to the right) while needle hub 500 includes protrusions (represented by lines running downwards to the right). The area where channels 403 and protrusions 503 interlock is represented by the cross-hatching.

In contrast to catheter assembly 200 shown in FIG. 2A, in catheter assembly 700, the positions of actuator 400 and needle hub 500 within catheter hub 701 substantially overlap. This overlapping increases the rigidity of catheter assembly 700.

The increase in the rigidity of catheter assembly 700 is primarily due to the spreading of the pivot point between catheter hub 701 and needle shield 702. For example, as shown in FIG. 7B, in response to a downward force (as represented by the arrow), the pivot point is spread along the length of the interface between actuator 400 and needle hub 500. In other words, the interlocked area created by channels 403 and protrusions 503 forms the pivot point for any flexing between catheter hub 701 and needle shield 702. Because this pivot point is substantially longer than the pivot point shown in FIG. 2B, a much greater force is required to cause flexing between catheter hub 701 and needle shield 702.

Also, because the interlocked area is created using channels 403 and protrusions 503 (i.e. by using a portion of the end of each component rather than overlapping the entire ends as shown in FIG. 3C), the increased rigidity can be provided without sacrificing the structural integrity of actuator 400.

Figure 8:
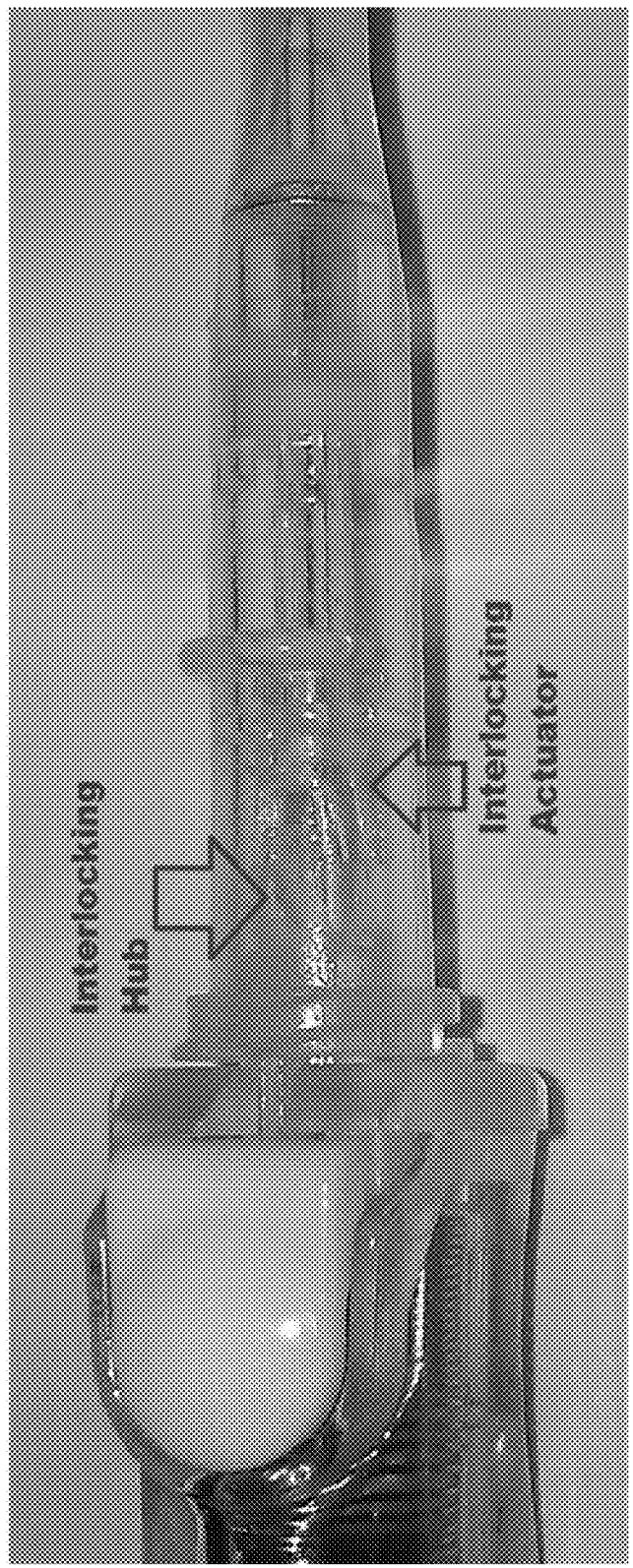
FIG. 8 illustrates a photo of an implementation of a catheter assembly that includes an actuator and needle hub configured in accordance with an embodiment of the invention.

FIG. 8 provides a photograph of an actual implementation of a catheter assembly in accordance with one or more embodiments of the invention. The tip of the interlocking actuator is identified and would be similar to proximal end 402 of actuator 400. Also, a protrusion is identified as extending past the identified tip of the interlocking actuator and into a channel of the interlocking actuator. A similar protrusion extends into a corresponding channel on the bottom of the depicted catheter assembly. Because the interlocking needle hub extends substantially into the catheter hub, and because the needle hub interlocks with the actuator, a greater amount of rigidity is provided between the needle shield and catheter hub.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A catheter assembly comprising:
    a catheter hub containing a septum actuator and a septum, the septum actuator configured to pierce the septum when a force is applied to the septum actuator, a catheter extending distally from the catheter hub; and
    a needle shield connected to the catheter hub, the needle shield containing a needle hub, the needle hub containing a needle, wherein the needle hub is initially positioned at a distal end of the needle shield such that the needle extends distally out through the catheter, and wherein, the needle hub is configured to retract proximally into the needle shield such that a distal end of the needle is captured within the needle shield;
    wherein the needle hub includes one or more protrusions that extend distally from an outer diameter of a distal end of the needle hub; and
    wherein the septum actuator includes one or more channels formed in a proximal end of the septum actuator, wherein, when the needle hub is positioned at the distal end of the needle shield, the one or more protrusions of the needle hub insert into the one or more channels thereby interlocking the needle hub with the septum actuator to provide greater rigidity between the catheter hub and the needle shield against vertical forces applied to the catheter assembly, wherein the one or more protrusions are configured to separate from the one or more channels to allow an access device to be connected to the catheter hub.

2. The catheter assembly of claim 1, wherein the septum actuator includes two channels and the needle hub includes two protrusions.

3. The catheter assembly of claim 2, wherein when the catheter assembly is positioned to be inserted into vasculature of a patient, the channels are positioned at a top and bottom of the septum actuator to provide greater rigidity against vertical forces applied to the catheter assembly.

4. The catheter assembly of claim 1, wherein the septum actuator is positioned completely within the catheter hub such that the needle hub extends into the catheter hub to interlock with the septum actuator.

5. The catheter assembly of claim 1, wherein an outer diameter of each protrusion matches an outer diameter of the corresponding channel.

6. The catheter assembly of claim 1, wherein the one or more protrusions extend into the catheter hub when the one or more protrusions insert into the one or more channels.

7. The catheter assembly of claim 1, wherein the catheter assembly is an intravenous catheter assembly.

8. The catheter assembly of claim 1, wherein the needle shield is detachable from the catheter hub to allow another access device to be connected to the catheter hub.

9. A catheter assembly comprising:
    a catheter hub having a distal end from which a catheter extends and a proximal end forming a proximal opening of a lumen, the lumen extending to the distal end of the catheter hub, the catheter hub including a septum positioned within the lumen and a septum actuator positioned proximal to the septum and configured to be forced through the septum to create a fluid pathway through the septum, a proximal end of the septum actuator including one or more channels; and
    a needle shield having a distal end configured to couple to the proximal end of the catheter hub, the needle shield containing a needle hub having a distal end from which a needle extends, the distal end of the needle hub including one or more protrusions corresponding to the one or more channels of the septum actuator, the needle hub having a first position and a second position within the needle shield, the one or more protrusions extending distally from an outer diameter of the needle hub;
    wherein, when the needle hub is in the first position, the one or more protrusions of the needle hub are inserted into the one or more channels of the septum actuator to provide greater rigidity between the catheter hub and the needle shield against vertical forces applied to the catheter assembly, and when in the second position, the needle hub is positioned towards a proximal end of the needle shield such that a distal end of the needle is contained within the needle shield, wherein the one or more protrusions are configured to separate from the one or more channels to allow an access device to be connected to the catheter hub.

10. The catheter assembly of claim 9, wherein the proximal end of the septum actuator includes two channels.

11. The catheter assembly of claim 10, wherein when the catheter assembly is positioned to be inserted into vasculature of a patient, the two channels are positioned at a top and bottom of the proximal end to provide greater rigidity against vertical forces.

12. The catheter assembly of claim 9, wherein the septum actuator is positioned completely within the catheter hub such that, when in the first position, the needle hub extends into the catheter hub.

13. The catheter assembly of claim 9, wherein an outer diameter of each channel matches an outer diameter of the corresponding protrusion.

14. The catheter assembly of claim 9, wherein at least one of the one or more channels is positioned at a side of the proximal end.

15. A catheter assembly comprising:
    a catheter hub having a distal end from which a catheter extends and a proximal end forming a proximal opening of a lumen, the lumen extending to the distal end of the catheter hub, the catheter hub including a septum positioned within the lumen and a septum actuator positioned proximal to the septum and configured to be forced through the septum to create a fluid pathway through the septum, a proximal end of the septum actuator including one or more channels; and a needle shield having a distal end configured to be selectively coupled to the proximal end of the catheter hub, the needle shield containing a needle hub having a distal end from which a needle extends, the distal end of the needle hub including one or more protrusions corresponding to the one or more channels of the actuator, the one or more protrusions extending from a distal-most surface of the distal end of the needle hub, the needle hub initially being positioned at the distal end of the needle shield such that the needle extends through the catheter hub and out through a distal end of the catheter, the needle hub further being configured to retract proximally into the needle shield after the needle has been used to insert the catheter into a vasculature of a patient;

wherein, prior to the needle hub being, retracted, the one or more protrusions of the needle hub are positioned within the one or more channels of the septum actuator to provide greater rigidity between the catheter hub and the needle shield against vertical forces applied to the catheter assembly, wherein the one or more protrusions are configured to separate from the one or more channels to allow an access device to be connected to the catheter hub.

16. The catheter assembly of claim 15, wherein the one or more protrusions comprise two protrusions.

17. The catheter assembly of claim 16, wherein when the catheter assembly is positioned to be inserted into vasculature of a patient, the two protrusions are positioned at a top and bottom of the distal end.

18. The catheter assembly of claim 15, wherein, prior to the needle hub being retracted, the one or more protrusions extend into the catheter hub.

19. The catheter assembly of claim 15, wherein the protrusions extend distally from an outer diameter of the needle hub.

* * * * *